United States Patent [19]

Bayston et al.

[11] Patent Number: 4,917,686

[45] Date of Patent: Apr. 17, 1990

[54] ANTIMICROBIAL DEVICE AND METHOD

[75] Inventors: Roger Bayston, London, England; Nancy J. Grove, Conifer, Colo.

[73] Assignee: Colorado Biomedical, Inc., Evergreen, Colo.

[21] Appl. No.: 123,922

[22] Filed: Nov. 23, 1987

Related U.S. Application Data

[63] Continuation-in-part of Ser. No. 809,235, Dec. 16, 1985, abandoned.

[51] Int. Cl.$^4$ .................................... A61M 5/325
[52] U.S. Cl. .................................................. 604/265
[58] Field of Search .................... 604/265, 267; 623/11

[56] References Cited

U.S. PATENT DOCUMENTS

| | | | |
|---|---|---|---|
| 4,343,788 | 8/1982 | Mustacich et al. | 424/78 |
| 4,392,848 | 7/1983 | Lucas et al. | 604/265 |
| 4,513,083 | 4/1985 | Hodes et al. | 530/395 |
| 4,605,564 | 8/1986 | Kulla et al. | 604/265 |
| 4,612,337 | 9/1986 | Fox, Jr. et al. | 604/265 |
| 4,686,124 | 8/1987 | Onohara et al. | 604/265 |
| 4,713,402 | 12/1987 | Solomon | 604/96 |

OTHER PUBLICATIONS

The Merck Index, 9th Edition, 1976, pp. 302, 303, 1068.
Bayston et al., J. Clin. Pathol. 198; 134:1057–1062, 1981.

Primary Examiner—C. Fred Rosenbaum
Assistant Examiner—Sharon Rose
Attorney, Agent, or Firm—Beaton & Swanson

[57] ABSTRACT

A medical device made from a material capable of being implanted in living tissue or transcutaneously inserted therein or of long term in-dwelling therein, which exhibits persistent antimicrobial activity in use, and containing a body of a synthetic or naturally occurring material having side surfaces and being capable of being swelled by penetration of a swelling agent and which has been subjected to such a swelling agent which contains completely dissolved therein at least one antimicrobial agent as a solute, the surfaces being contacted by such swelling agent for a sufficient period of time to promote swelling of the matrix of a body of material and thereby permit diffusion and migration of the solution containing the selected antimicrobial agent solute into the interstitial spaces of the body of material at the molecular level by the action of the swelling agent within the body of material, and the solvent being capable of being removed from the solute in the body of material by evaporation and after removal of the solvent the body of material being capable of returning substantially to its original size and shape with the antimicrobial agent substantially uniformly deposited therein for subsequent continuous migration to and diffusion through the surfaces.

14 Claims, No Drawings

ANTIMICROBIAL DEVICE AND METHOD

BACKGROUND OF THE INVENTION

This is a continuation-in-part of prior copending application Ser. No. 809,235 filed Dec. 16, 1985, now abandoned.

Implanted medical devices which involve catheters, valves, molded parts, etc., and which must reside totally or partially within the human body for relatively long periods of time have historically been plagued with the problem of infection. Examples of this group of devices include hydrocephalus shunts and central venous catheters. Colonization of bacteria on the interior surfaces of the catheter or other part of the device can produce serious patient problems, including the need to remove and/or replace the implanted device and secondary infective conditions.

A considerable amount of attention and study has been directed toward attempting to prevent such colonization by the use of antimicrobial agents, such as antibiotics, bound to the surface of the materials employed in such devices. In such attempts the objective has been to produce a sufficient bacteriostatic or bacteriocidal action to prevent colonization.

These prior attempts have utilized a wide variety of antimicrobial agents, methods for their application and adherence to a wide variety of substrate materials, including silicone elastomers, polytetrafluoroethane, polyesters, polyethylene, and latex rubber.

Exemplary of the extensive investigation into this problem by researchers are the following publications, which are incorporated herein by reference.

BAYSTON, R., and MILNER, R. D. G., "Antimicrobial Activity of Silicone Rubber Used in Hydrocephalus Shunts, after Impregnation with Antimicrobial Substances" *J Clin Pathol* 1981, 134:1057–1062.

BAYSTON, R., "Effect of Antibiotic Impregnation on the Function of Slit Valves Used to Control Hydrocephalus" *Z. Kinderchir.* Band 31, Heft 4, December 1980, pp 353–359.

HARVEY, R. A.: GRECO, R. S.: "The noncovalent bonding of antibiotics to a polytetrafluoroethylenebenzalkonium graft." *Ann Suro* 194:642–7, 1981.

TROOSKIN, STANLEY A., DONETZ, ANTHONY P.; HARVEY, RICHARD A.; and GRECO, RALPH S. "Prevention of catheter sepsis by antibiotic bonding", *Surgery*, 1984. pp 547–551.

DONETZ, A. P., HARVEY, R.A., GRECO, R. S.: Stability of antibiotics bound to polytetrafluoroethylene with cationic surfactants. *J Clin Microbiol* 19:1–3, 1984.

Therefore, prior attempts have unfortunately not produced the optimum results. The major drawback has been and remains, that antimicrobial activity provided by certain surface treatments is relatively short lived. This observation has supported the theory that the agents and methods used provide only a temporary surface bonding of the selected agent to the device.

In addition, it has not been demonstrated that a surface treated device can be successfully sterilized by known methods without deleteriously affecting the antimicrobial agent or its bond to the surface of the material of which the device is made. That is, subsequent sterilization of surface bonded agents tends to shorten the time of antimicrobial activity and, in addition, may produce byproducts that are harmful to body tissue.

It is therefore an objective of the present invention to provide a method by which antimicrobial agents can be incorporated into a wide variety of commonly used elastomers or the like, so as to provide a relatively longer term of protection against bacterial colonization on the surface of those materials without accompanying harmful side effects.

It is a further objective to provide a article exhibiting the foregoing advantages that is capable of being sterilized before use and still retain those advantages.

BRIEF SUMMARY OF THE INVENTION

The present invention provides a medical device made from a polymeric material such as silicone elastomers or the like capable of being implanted in living tissue, which material has been treated to exhibit persistent antimicrobial activity in use of the device, and is capable of being swelled by penetration of a swelling agent and which has been subjected to such a swelling agent which contains completely dissolved therein at least one or more antimicrobial agent(s) as a solute, the surfaces being contacted by such swelling agent for a sufficient period of time to promote swelling of the matrix of a body of material and thereby permit diffusion and migration of the solution containing the selected antimicrobial agent solute into the intermolecular spaces of the body of material by the action of the swelling agent within the body of material, and the solvent being capable of being removed from the solute in the body of material by evaporation and after removal of the solvent the body of material being capable of returning substantially to its original size and shape with the antimicrobial agent(s) substantially uniformly deposited therein for subsequent continuous migration to and diffusion through the surfaces.

The present invention also provides a method of infusing antimicrobials into the body of implantable medical devices containing a silicone elastomeric body of material and comprising the steps of completely contacting the surfaces of such device with a solution consisting of a swelling agent and at least one antimicrobial agent dissolved therein; maintaining contact between the solution and the surfaces for a sufficient period of time for the solution to completely swell the body of polymeric material and to diffuse the solution into the enlarged intermolecular spaces of the matrix provided by the swelling; evaporating the solvent from the solution to thereby substantially uniformly deposit the antimicrobials within the body of polymeric material while causing the material to return substantially to its original physical shape and condition; rinsing the treated surfaces; and sterilizing the treated body of the material prior to use.

The present invention utilizes a swelling agent which (1) is capable of increasing the intermolecular spaces of silicone elastomers or other polymeric materials or late;; and (2) which is capable of dissolving selected antimicrobial agents without substantially chemically altering them under conditions and in a manner to permit the infusion of the antibacterial agents selected into the swelled material substantially uniformly and in sufficient amounts to provide for a prolonged significant level of antimicrobial activity when the infused material is subsequently implanted in the body. In vitro tests have shown that the present invention provides effective protection against excessive bacterial challenge in silicone elastomer tubing for at least 28 days during which a nutrient solution is perfused at 37° C. through the central lumen of the tubing. Tests have also shown that silicone elastomer treated by the methods of the present invention retain antimicrobial activity after at least 20 months of shelf storage.

DETAILED DESCRIPTION OF THE INVENTION

In general, the medical device of the present invention comprises a body of substantially homogeneous polymeric material such as silicone elastomer or the like. One or more antimicrobial agent(s) are substantially uniformly dispersed throughout the body of polymeric material and provide a substantially uniform molecular dispersion of the antimicrobial agent(s) within the intermolecular spaces of the body of polymeric material. The body of polymeric material and the antimicrobial agent therein effectively provide a solid solution of molecules of polymeric material and molecules of antimicrobial agent(s) having a concentration such as to cause diffusion of the molecules of the antimicrobial agent(s) toward and through the side surfaces of the body of polymeric material, when in use, for sufficient periods of time to provide effective protection against colonization after implant in the human body.

The preferred antimicrobials used in the process of the present invention are the following: (1) rifampin which is a semisynthetic antibiotic derivative of rifamycin B (specifically, rifampin is the hydrazone, 3-(4-methyl-1-piperazinyliminomethyl)-rifampinSV.); and (2) clindamycin hydrochloride. These preferred agents are preferably used in combination as solute and together they provide superior penetration and persistent antimicrobial activity in devices treated according to the present invention with a broad spectrum covering most strains of gram positive bacteria causing the majority of infections in medical devices such as a hydrocephalus shunt. The agents may also be used as a colloidal suspension or emulsion The method of manufacture of the medical device comprises subjecting all surfaces of the body of polymeric material to a solution containing a suitable swelling agent (solvent), such as hexane, toluene, xylene or preferably chloroform, and the antimicrobial agent(s) (solute) for a sufficient time to enable penetration and swelling of the entire body of polymeric material and substantially homogeneous dispersion of the antimicrobial agent(s) throughout the body of polymeric material within the enlarged intermolecular spaces thereof. The swelling agent is thereafter removed by evaporation to reverse swelling while retaining the antimicrobial agent(s) in a substantially uniform dispersion in the intermolecular spaces throughout the body of polymeric material so that the molecules of the antimicrobial agent(s) are essentially in solid state solution with the molecules of the body of the polymeric material an will thereafter migrate toward the surfaces of the body of the polymeric material and through the surfaces thereof solely by molecular diffusion. After the swelling agent is removed, the device is suitably sterilized either by ethylene oxide or gamma irradiation or low temperature steam autoclaving, but preferably in an autoclave with the device being subjected to steam heat at a temperature of 250o F and a pressure of 15 psi above atmospheric to obtain the advantageous results hereinafter described.

One objective is that there should be enough of the antimicrobial agent(s) to maintain the desired level of activity for the desired length of time. Another objective is that there should be insufficient antimicrobial agent(s) to cause toxicity or other deleterious effects to the implant or to its function or to the recipient. In general, the period of risk for infection resulting from an operation to implant a device may vary from the moment of implantation to any time during the life of the device after the operation. Thus, it is advantageous to be able to control the amount and the dispersion of the antimicrobial agent(s) within the matrix of the elastomer. In order to obtain the desired results, the material from which the device is made must be such as to retain the antimicrobial agent in a manner which prevents release of an oversupply of the agent while at the same time providing a continuous, effective supply of the agent at the surface of the device for a sufficient length of time. An effective amount of antimicrobial agent(s) (e.g. 0.1% to 1.0% by weight of each to volume of solvent) is employed dependent upon the size and shape of a particular medical device and upon the kind and wall thicknesses of the selected polymeric material. In the presently preferred embodiments, for a device such as a shunt or a catheter, the amount of antimicrobial agent(s) is preferably about 0.1% to 0.2% by weight of each agent to volume of solvent.

It has been unexpectedly discovered that good retention of satisfactory amounts of the antimicrobial agent(s) can be maintained without adversely affecting antimicrobial activity when the device is sterilized, preferably in an autoclave apparatus, with the body of the polymeric material being subjected to steam heat at a temperature of 250o F and a pressure of 15 psi above atmospheric for approximately 30 minutes; and this sterilization process, though not others, has a beneficial effect o the diffusion characteristics. The temperature, pressure and time may be varied in accordance with size, shape and other characteristics of the device to achieve complete sterilization.

The infusion treatment used herein is carried out in specially made glass impregnation chambers which conform to the shape of the device which has been selected for infusion processing, at its maximum swelling. These treatment chambers are designed to accommodate the device to be infused. A sufficient quantity of solution is used to provide contact between the solution and all surfaces of the device.

Charging the Material with Antimicrobial Agent

The clean, dry device to be impregnated is submerged in antimicrobial solution and primed so as to expose the interior and exterior surfaces of the device to the solution and to expel all air bubbles. The device is secured in the chamber, because as the silicone rubber device swells in the charging solution, it becomes buoyant and will rise sufficiently to project out of the charging chamber if it is not properly secured.

The processing time starts when the tube is fully submerged. The chamber is covered to minimize the evaporation of the solvent from the charging solution during treatment. The duration of the treatment is about 30 minutes to one hour of contact with the solution, although the swelling itself may be substantially completed in approximately 10 minutes. The charging chamber is checked visually during processing to make sure that the device has remained submerged.

At the end of the processing period the device is carefully removed from the chamber allowing the liquid inside the device to drain into the chamber. The swelled silicone rubber is mechanically vulnerable at this stage and tears easily. Therefore, it must be handled gently. After it has been removed from the charging chamber, the treated device is immediately immersed in an ethyl alcohol bath. This rinse reduces the spotting of the antimicrobial material on the outside of the device as it dries, but does not significantly reduce the level of the antimicrobial activity. The device is then suspended in a vertical position, and permitted to air dry at room temperature (21o C) The device is then allowed to outgas in this position overnight. At room temperature the device will usually have regained its initial size and shape within 10 minutes after removal from the charging chamber.

After outgassing, the treated device is briefly washed in running tap water and rinsed in deionized water. It is again air dried for a short period in a warm dry air oven at a temperature not exceeding 200° F. The treated device is then sterilized by sufficient autoclaving at 250° F. for 30 min at 15 psi above atmospheric pressure as previously described. It was discovered as a part of the present invention that autoclaving is not only satisfactory but also provides new and unexpected results in that there is better retention of the antimicrobial agent(s) within the body of polymeric material. After sterilization, the treated device should be stored in the dark at room temperature.

The antimicrobial(s) used to impregnate the device are best prepared in solutions immediately before use. Because of the potential light-sensitive nature of the agent(s) and the volatile nature of the solvents, great care must be taken not to expose the solutions to direct sunlight or to store them in solution for any prolonged period prior to use. The solutions are discarded immediately after use.

The antimicrobial(s) are stored in a dry form according to the manufacturers' recommendations Immediately prior to use they are weighed on an analytical balance to give a concentration typically 0.1% or more of each by weight/volume. The solutes are dissolved in an appropriate solvent such as chloroform. Only glass beakers and glass volumetric flasks are used with the solvent-based solutions.

SUMMARY OF BENEFITS AND RESULTS

In summary, the device is made of silicone elastomer having a size and shape which can be temporarily expanded to enlarge the normal intermolecular spaces to enable penetration of a treatment solution, including a removable expanding agent and antimicrobial agent(s), and which can be subsequently contracted to substantially the normal size and shape and substantially normal molecular structure by removal of the expanding agent, while retaining a substantial quantity of chemically intact antimicrobial agent(s) within the substantially normal molecular structure.

In use, it is believed that the antimicrobial agent(s) within the body of polymeric material ar released to and through the surfaces by solid state diffusion Because of the molecular structure of the polymer and the intimate molecular association of the antimicrobial agent(s) therewith, the diffusion of these agent(s) occurs at a rate which provides antimicrobial efficacy at the surfaces of the device for a substantial period of time.

Silicone elastomers of varying consistencies and/or configurations, when processed according to the invention, demonstrate the ability to (1) absorb antimicrobials into their intermolecular spaces and retain chemically intact antimicrobials within their intermolecular spaces; (2) release antimicrobials over time through constant diffusion of the antimicrobial to and through their surfaces; (3) retain antimicrobial activity after sterilization; (4) be capable of being sterilized by autoclaving without loss of antimicrobial activity and with enhanced retention of antimicrobials; (5) retain antimicrobial activity over time of storage; (6) provide effective protection against excessively high bacterial challenge; and (7) when processed according to the invention and implanted in living tissues, demonstrate no harmful side effects to surrounding tissue(s) and/or organs.

Thus, surgically implanted silicone elastomer devices such as hydrocephalus shunts, when processed according to the invention, will resist bacterial contamination introduced at the time of surgery which can lead to the colonization of the implant and its ultimate failure, removal and replacement; and will provide longer period of protection against colonization by introduced bacteria due to the constant diffusion of antimicrobial to the surfaces of the device.

It is contemplated that the inventive concepts herein described may be variously otherwise embodied and it is intended that the appended claims be construed to include alternative embodiments of the invention except insofar as limited by the prior art.

What is claimed is:

1. A medical device made from a material capable of being implanted in living tissue and of long indwelling therein, which exhibits persistent antimicrobial activity in use, and comprises:

a body of a polymeric material which is capable of being swelled by a swelling agent and which has been subject to such a swelling agent which contains completely dissolved therein one or more antimicrobial agents as a solute, said body being contacted by such swelling agent for a sufficient period of time to promote swelling of the body of material to enlarge the normal size and intermolecular spaces therewithin thereby causing diffusion and migration of the solution containing the selected antimicrobial agent(s) into the enlarged intermolecular spaces of the body of material by the action of the swelling agent within the body of material and said solvent being removed from said solute in the matrix of the body of material by evaporation with said solute remaining in the intermolecular spaces of the body of material and after removal of said solvent said body of material returning substantially to its original size and shape and having substantially normal intermolecular spaces with said antimicrobial agent substantially uniformly deposited therein for subsequent continuous molecular migration to and molecular diffusion through the surfaces to provide persistent antimicrobial activity at the surfaces of during use in the human body, said medical device subject to autoclaving prior to use; and said polymeric material and said antimicrobial agent(s) selected so that the rate of continuous molecular migration and molecular diffusion remains the same or is retarded by the effects of autoclaving.

2. The medical device of claim 1 wherein: the selected material is a silicone elastomer.

3. The medical device of claims 1 and 2 wherein: the swelling agent is chloroform or its chemical homologs.

4. The medical device of claim 3 wherein: the antimicrobial agent is selected from the group consisting of rifampin, clindamycin hydrochloride and mixtures thereof.

5. The medical device of claim 4 wherein: each selected antimicrobial is dissolved in the swelling agent in an amount of about 0.1% to 1.0% weight by volume of the swelling agent.

6. The medical device of claim 1 wherein: said autoclaving occurs at about 250° F. and at a pressure of about 15 psi above atmosphere.

7. A method of infusing antimicrobials into the body of implantable and long in-dwelling medical devices containing a body of elastomer material comprising the steps of:
   completely contacting the surfaces of the body of elastomer with a solution comprising a swelling agent as a solvent and at least one antimicrobial agent as a solute dissolved therein, said elastomer and said at least one antimicrobial agent selected so that the rate of diffusion of the antimicrobial agent out of the medical device will remain the same or be retarded by the effects of autoclaving.
   maintaining contact between the solution and the surfaces for a sufficient period of time for the solution to completely penetrate and swell and to enlarge the normal intermolecular spaces of the body of material and to diffuse the solution into the enlarged intermolecular spaces provided by the swelling;
   evaporating the solvent from the solution and to thereby deposit and retain the antimicrobial agent within the intermolecular spaces of the body of elastomer while causing the body of material to return substantially to its original physical shape and condition with substantially normal intermolecular spaces; and
   rinsing the surfaces of the treated body of material and autoclaving the treated body of material prior to use.

8. The method of claim 7 wherein: the antimicrobial agent is selected from the group of broad spectrum antibiotics consisting of rifampin, clindamycin hydrochloride and mixtures thereof and is dissolved in chloroform.

9. The method of claim 7 or 8 wherein: said autoclaving occurs at about 250° F. and at about 15 psi above atmospheric pressure.

10. An antimicrobial composition capable of being infused into the body of a medical device made of silicone elastomer or the like comprising a swelling agent for the silicone elastomer, a solvent, and solute consisting of rifampin and clindamycin hydrochloride, said swelling agent being chloroform or one of its homologs.

11. A medical device for use in the human body and comprising:
   a body of silicone elastomer having a matrix of polymeric molecules;
   two antimicrobial agents substantially uniformly dispersed throughout said body of polymeric material and providing a substantially uniform molecular dispersion of said antimicrobial agents within the normal intermolecular spaces of said body of silicone elastomer; and
   said body of silicone elastomer and said antimicrobial agents therein effectively providing a solid solution of molecules of polymeric material and molecules of antimicrobial agent having a concentration and concentration distribution of antimicrobial agent such as to cause solid state diffusion of the molecules of the antimicrobial agent toward and through the intermolecular spaces of the body of polymeric material for sufficient period of time to provide effective protection against infection after implant in the human body, the rate of said solid diffusion having remained the same or been retarded by autoclaving such device.

12. The invention of claim 11 wherein: the swelling agent is chloroform or a chemical homolog.

13. The invention of claim 11 and 12 wherein: the antimicrobial agents are selected from the group consisting of rifampin, clindamycin hydrochloride and mixtures thereof.

14. The invention of claim 13 wherein: each of the antimicrobial agents are dissolved in chloroform in the amount of 0.1% to 1.0% by weight of agent to volume of chloroform.

* * * * *